US009429557B2

(12) United States Patent
Bachmann et al.

(10) Patent No.: US 9,429,557 B2
(45) Date of Patent: Aug. 30, 2016

(54) METHOD FOR PRODUCING WEB-LIKE MATERIAL

(75) Inventors: Bernhard Bachmann, Bielefeld (DE); Rainer Ueckerdt, Berlin (DE); Hermann Penner, Bielefeld (DE); Dieter Becker, Georgsmarienhuette (DE); Stefan Rodewald, Bielefeld (DE); Christian Elsner, Leopoldshoehe (DE)

(73) Assignee: Mitsubishi HiTec Paper Europe GmbH, Flensburg (DE)

( * ) Notice: Subject to any disclaimer, the term of this patent is extended or adjusted under 35 U.S.C. 154(b) by 730 days.

(21) Appl. No.: 13/813,129

(22) PCT Filed: Jul. 12, 2011

(86) PCT No.: PCT/EP2011/061814
§ 371 (c)(1),
(2), (4) Date: Apr. 10, 2013

(87) PCT Pub. No.: WO2012/013484
PCT Pub. Date: Feb. 2, 2012

(65) Prior Publication Data
US 2015/0309005 A1    Oct. 29, 2015

(30) Foreign Application Priority Data
Jul. 30, 2010   (EP) .................... 10171493

(51) Int. Cl.
*G01N 37/00* (2006.01)
*G01N 33/34* (2006.01)
*D21G 9/00* (2006.01)
*G05B 19/418* (2006.01)
*G06F 11/00* (2006.01)

(52) U.S. Cl.
CPC .......... *G01N 33/346* (2013.01); *D21G 9/0045* (2013.01); *G05B 19/41875* (2013.01); *G05B 2219/32368* (2013.01)

(58) Field of Classification Search
CPC .......... G01N 33/346; G05B 19/41875; G05B 2219/32368
See application file for complete search history.

(56) References Cited

FOREIGN PATENT DOCUMENTS

| EP | 1 473 407 | A1 | 11/2004 |
| EP | 1473407 | A * | 11/2004 |
| WO | WO 03/072 874 | A1 | 9/2003 |
| WO | WO 03/072874 | A1 * | 9/2003 |
| WO | WO 2010/080 869 | A1 | 7/2010 |
| WO | WO 2010/080869 | A1 * | 7/2010 |

* cited by examiner

*Primary Examiner* — Phuong Huynh
(74) *Attorney, Agent, or Firm* — Cozen O'Connor

(57) ABSTRACT

A method for the production and/or processing of a web-shaped material, particularly paper, with at least one measuring system which records m measurement values $y_{ik}$ per measurement position over at least a portion of the width s of the web-shaped material at n different measurement positions within a fixed time interval $\Delta t$. The method is characterized in that the method includes determining a rational quality number Q, the value of which for a quality of the web-shaped material that is considered acceptable lies within an acceptance range which is to be empirically determined for the production process and which has a lower limit U and an upper limit O, where U and O are in each case rational numbers.

11 Claims, 2 Drawing Sheets

Transverse profile of the respective totality of all mean values $\bar{y}_i$ for the n = 512 measurement positions for m = 60 traverses with Q = 4.5, that is, outside of the empirically determined acceptance range of U = 2.2 ≤ Q ≤ O = 4.2.

Transverse profile of the respective totality of all mean values $\bar{y}$ for the n = 512 measurement positions for m = 60 traverses with Q = 4.5, that is, outside of the empirically determined acceptance range of U = 2.2 ≤ Q ≤ O = 4.2.

Transverse profile of the respective totality of all mean values $\overline{y_i}$ for the n = 512 measurement positions with m = 60 traverses with Q = 2.7, that is, within the empirically determined acceptance range of U = 2.2 ≤ Q ≤ 4.2.

METHOD FOR PRODUCING WEB-LIKE MATERIAL

PRIORITY CLAIM

This is a U.S. national stage of PCT International Application No. PCT/EP2011/061814, filed on 12 Jul. 2011, which claims priority to German Application No. 10171493.9, filed 30 Jul. 2010, the contents of which are incorporated herein by reference in its entirety.

BACKGROUND OF THE INVENTION

1. Field of the Invention

The invention is directed to a method for the production and/or processing of a web-shaped material, particularly paper, with at least one preferably traversing measuring system which records m measurement values per measurement position over the width s of the web-shaped material at n different measurement positions within a fixed time interval $\Delta t$.

2. Description of the Related Art

Measuring systems of the type mentioned above have been known for many years particularly in the paper producing industry, where they are used for ongoing process control and quality control.

Problems arise in the previously known systems due to the fact that the known measuring systems ultimately generate an enormous quantity of individual measurement values or measurement profiles in the form of graphs showing a plurality of recorded measurement values, and these measurement values or measurement profiles are subsequently subjectively interpreted typically by production supervisors. In so doing, the measurement profiles which show either measurement values which are recorded one after the other at the same measurement position (longitudinal profile) or measurement values of adjacent measurement positions transversely over the web of the web-shaped material (transverse profile) are allotted particular importance because they allow a highly focused search for tendencies in production.

Precisely with this in mind, European Published Patent Application No. 1 473 407 A1 suggests a method for generating two-dimensional charts—see FIGS. 1 and 2 of the cited document—of webs of a sheet-like material such as paper or foil which have been generated beforehand. On the one hand, each chart for illustrating longitudinal profiles and transverse profiles of different measurement parameters has a very high information content; on the other hand, for this very reason, they are subject to a variety of possible interpretations. The second approach in the above-cited document, to show overlapping and possibly also cyclical events in production by means of a plurality of transverse profiles, points in exactly the same direction: a large quantity of numerical values is generated which are ideally portrayed two-dimensionally and which must subsequently be interpreted, which requires a great deal of individual experience.

The subject matter of the somewhat older International Published Patent Application No. 03/072 874 A1 is ultimately directed to a control device for optimizing fiber orientation in paper production. To this end, the previously recorded measurement values for fiber orientation with respect to the feed direction and transverse direction of the paper web through the machine is fed to the control device. Then, by manipulating the set values of the machine, the control device is supposed to optimize the fiber orientation for the paper web to be produced by means of known fuzzy logic. The aim of this known document is not to provide quality numbers as a decision-making basis for determining papers which are or are not suitable for use.

Finally, International Published Patent Application No. 2010/080 869 A1 suggests a method for providing a probability model in which probability profiles are computed from a plurality of recorded measurement value profiles for previously determined and adjusted machine parameters in order to facilitate decisions on the part of the machine attendants for the optimal setting of machine setpoints based on the provided probability profiles. Again, in no way does this document aim at providing quality numbers as a simple basis for decision for determining papers which are or are not suitable for use.

To summarize, the methods known from the prior art assessed above have previously been suitable for using data obtained from measurement profiles directly within the internal production process or, more so, to readily display these data particularly in complicated two-dimensional graphs. The information obtained in this way is diverse, but is extremely difficult to interpret and analyze. But even when the production supervisors whose job is to interpret recorded measurement profiles have many years of on-the-job experience, the results of this interpretation are still often speculative and always highly subjective and are therefore dependent upon attitude and/or personality and are ultimately also not reproducible. In particular, a persistent problem consists in that a uniform production control based on the subjective interpretation of measurement profiles depends upon the individual interpretive ability of particular persons whose departure from the enterprise represents an ever-present risk.

For an enterprise, this dependence on persons is always highly risky. It is also always unsatisfactory to base industrial production on measurement profiles which are interpreted subjectively and under time pressure.

SUMMARY OF THE INVENTION

Therefore, an object of the present invention is provide a method for producing a web-shaped material, which method is defined and guided within the ongoing process exclusively by comprehensible parameters which are defined beforehand and without time pressure and which, consequently, is not based on speculative, subjective interpretation of measurement profiles depending on the individual interpretive ability of particular persons.

This object is met by means of a method for the production and/or processing of a web-shaped material, particularly paper, with at least one measuring system which records m measurement values $y_{ik\ (i=1,\ \ldots,\ n;\ k=1,\ \ldots,\ m)}$ per measurement position within a fixed time interval $\Delta t$ over at least a portion of the width s of the web-shaped material at n different measurement positions $x_{i\ (i=1,\ \ldots,\ n)}$, wherein the method is characterized in that the method includes determining a rational quality number Q, the value of which for a quality of the web-shaped material that is considered acceptable lies within an acceptance range which is to be empirically determined for the production process and which has a lower limit U and an upper limit O, where U and O are in each case rational numbers subject to the condition according to:

$$U \leq Q \leq O, \qquad \text{Formula 1:}$$

where the value of the quality number Q is calculated as a function of moments $M_i$ according to formula 2, where:

$$Q = f(M_i), \qquad \text{Formula 2:}$$

and where the moments $M_i$ are calculated from the function value of the cubic spline function $S(x)$ for the n different measurement positions according to formula 3, where:

$$S(x)=\alpha_i+\beta_i\cdot(x-x_i)+\gamma_i\cdot(x-x_i)^2+\delta_i\cdot(x-x_i)^3, \quad \text{Formula 3:}$$

where:
x is a control variable in direction of the width s of the web-shaped material in interval $[x_i, x_{i+1}]$
$x_{i\ (i=1,\ \ldots,\ n)}$ are the measurement positions, also referred to in mathematics as knots of the cubic spline function, for moments $M_i$,
and wherein, based on the measurement values $y_{ik}$ which serve as a basis and using the preceding formula 3 as representation of the function value of the cubic spline function $S(x)$, formula 4 applies to the moments $M_i$, where $$M_i=2\cdot\gamma_{i\ (i=1,\ \ldots,\ n-1)}, M_n=2\cdot\gamma_{n-1}+\delta_{n-1}\cdot(x_n-x_{n-1})_{[41]}. \quad \text{Formula 4:}$$

A measuring system for the method suggested herein is preferably designed to be traversing. In this respect, by the word "traversing" is meant within the meaning of the invention:
either that a measuring system is moved back and forth transversely over at least a portion of the width s of the web-shaped material so that the m different individual measurement values $y_{ik}$ are recorded gradually as the individual n different measurement positions are reached,
or that a measuring system has n different measuring heads which are interrogated in sequence until all m measurement values $y_{ik}$ for all n different measurement positions have been recorded successively,
or that a combination of the two aforementioned measurement value recordings is used.

DETAILED DESCRIPTION OF THE PREFERRED EMBODIMENTS

Figure 1:
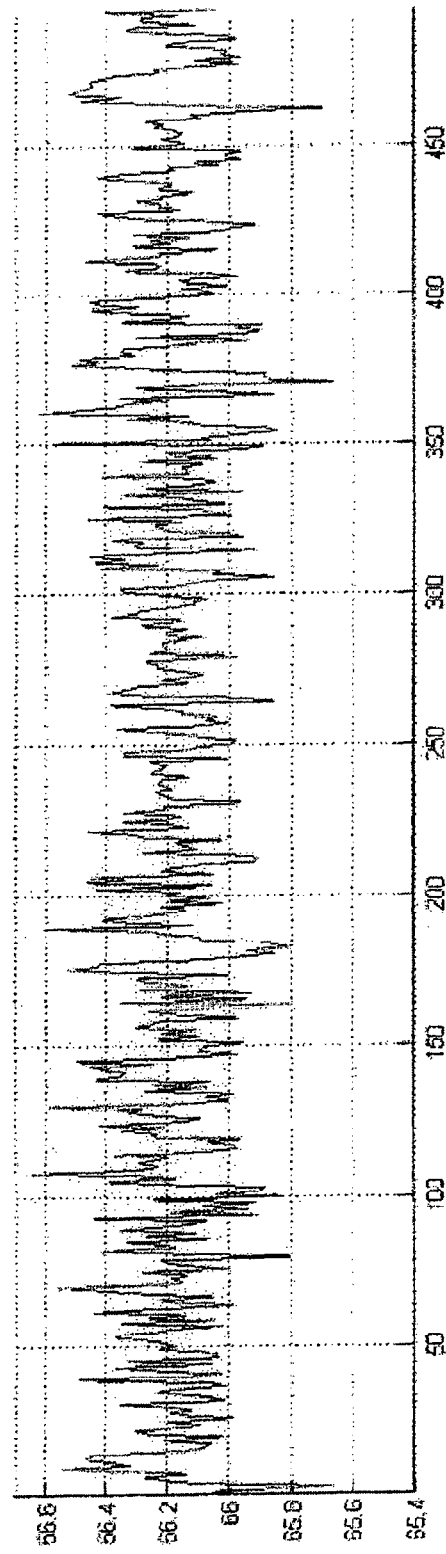
FIG. 1 is a diagram of a first recorded transverse profile.

The method proposed herein is implemented first in that measurement values $y_{ik}$ are recorded within a fixed time interval $\Delta t$ over at least a portion of the width s of the web-shaped material at n different measurement positions, wherein m measurement values $y_{ik\ (i=1,\ \ldots,\ n;\ k=1,\ \ldots,\ m)}$ are recorded per measurement position in each instance. The fact that the individual measurement values $y_{ik}$ are recorded by means of a preferably traversing measuring system means that one measurement value $y_{ik}$ is recorded in each instance per traversal of each of the individual n different measurement positions: these measurement values $y_{ik}$ which are recorded once in each instance then collectively form a transverse profile over at least a portion of the width s of the web-shaped material. Accordingly, with a total of m traverses, the measurement values for m transverse profiles are recorded.

Finally, notwithstanding the manner in which the measurement values $y_{ik}$ have been recorded by means of the preferably traversing measuring system, there are m individual measurement values $y_{ik}$ for all n measurement positions.

The method proposed herein preferably provides for the formation of the respective arithmetic mean according to formula 5, where:

$$\bar{y}_i = \sum_{k=1}^{m} \frac{y_{ik}}{m}, \quad \text{Formula 5}$$

wherein this arithmetic mean is to be formed for all n measurement positions from the associated m individual measurement values $y_{ik}$ so that finally there is exactly one mean $\bar{y}_i$ for each individual measurement position n.

The totality of all mean values $\bar{y}_i$ for all n measurement positions then collectively forms exactly one transverse profile over at least a portion of the width s of the web-shaped material. For this exactly one transverse profile, the fitting cubic spline function formed of n subfunctions is now determined automatically, preferably by means of mathematical calculation programs, for all n measurement positions according to formula 3:

$$S(x)=\alpha_i+\beta_i\cdot(x-x_i)+\gamma_i\cdot(x-x_i)^2+\delta_i\cdot(x-x_i)^3 \text{ in interval} \\ [x_i,x_{i+1}] \quad \text{Formula 3:}$$

within which:
x is a control variable in direction of the width s of the web-shaped material in interval $[x_i, x_{i+1}]$
$x_{i\ (i=1,\ \ldots,\ n)}$ are the measurement positions, also referred to in mathematics as knots of the cubic spline function, for moments $M_i$.

According to formula 3, $S(x)$ is a function value of the cubic spline function, wherein this function value $S(x)$ in the measurement positions $x_{i\ (i=1,\ \ldots,\ n)}$ is predetermined in each instance by the arithmetic mean of the associated m individual measurement values for this measurement position $$\bar{y}_i = \sum_{k=1}^{m} \frac{y_{ik}}{m}$$

according to formula 5. Accordingly, the result of the mathematical calculation program for determining the fitting cubic spline function formed of n subfunctions is the determination of all variables $\alpha_{i\ (i=1,\ \ldots,\ n)}$, $\beta_{i\ (i=1,\ \ldots,\ n)}$, $\gamma_{i\ (i=1,\ \ldots,\ n)}$ and $\delta_{i\ (i=1,\ \ldots,\ n)}$.

To determine the curve behavior, the second derivative must now be taken for the entire cubic spline function. The second derivatives per interval are given in each instance by formula 6.

$$S''(x_i)=2\cdot\gamma_i+6\cdot\delta_i\cdot(x-x_i) \text{ in interval}[x_{i-1},x_i] \quad \text{Formula 6:}$$

However, within the knots for the cubic spline function, i.e., the measurement positions according to the invention, $x=x_i$ applies. Therefore, the subtraction $(x-x_i)$ equals zero for all measurement positions within formula 6.

Applied to formula 6, the second derivatives at the knots, i.e., the n measurement positions according to the invention (see above), are given by formula 7:

$$S''(x_i)=2\cdot\gamma_{i\ (i=1,\ \ldots,\ n)}, S''(x_n)=2\cdot\gamma_{n-1}+\delta_{n-1}\cdot(x_n-x_{n-1}). \quad \text{Formula 7:}$$

Generally, and thus within the present application, the second derivatives according to formula 7 can be referred to as moments $(M_i)$ of the cubic spline function in the n measurement positions. In addition, it is true for natural cubic spline functions by definition that $M_1=M_n=0$. The use of natural cubic spline functions within the method according to the invention for determining a rational quality number Q is particularly preferred.

Thus the final result of the foregoing calculations gives n moments $(M_i)$, all of which satisfy formula 4 and formula 7, respectively. According to the invention, the value of the quality number Q according to formula 2 is a function of these moments ($M_i$), which means that the quality number Q is calculated from the n moments ($M_i$).

Various functions are considered for calculating the quality number Q from moments ($M_i$), where the following functions are preferred:
  maximum value of the absolute values (maximum norm) of all moments ($M_i$),
  square root of the sum of the squares of moments $M_i$, (Euclidean norm) given by formula 8:

$$Q = \sqrt{\sum_{i=1}^{n} |M_i|^2} \qquad \text{Formula 8}$$

variance of the moments ($M_i$),
  σ-rules of any degree of moments $M_i$ (σ-value, 2σ-value, 3σ-value, ...),
  mean of the moments ($M_i$).

Within the meaning of the present invention, it is highly preferable that the sum of the absolute values of the moments $M_i$ (1-norm) is used as function to calculate the quality number Q from the moments ($M_i$), i.e., when formula 9 is given for calculating the quality number Q from the moments ($M_i$):

$$Q = \sum_{i=1}^{n} |M_i| \qquad \text{Formula 9}$$

To ensure that the quality number Q is decoupled from the absolute numbers of the measurement values, it is particularly preferable that the values resulting directly in accordance with the preceding suggestions for calculating the quality number Q from moments ($M_i$) are divided by the mean $$\sum_{i=1}^{n} \frac{\bar{y}_i}{n}.$$

Accordingly, it is highly preferable that the function for calculating the quality number Q from the moments $M_i$ is the sum of the absolute values of the moments $M_i$ divided by the mean $$\sum_{i=1}^{n} \frac{\bar{y}_i}{n}$$

according to formula 10:

$$Q = \frac{\sum_{i=1}^{n} |M_i|}{\sum_{i=1}^{n} \frac{\bar{y}_i}{n}} \qquad \text{Formula 10}$$

It is highly preferable that the method proposed herein for the production and/or processing of a web-shaped material, particularly paper, with the at least one preferably traversing measuring system additionally includes a refining process which is modified and/or prevented or stopped when the quality number Q for the web-shaped material to be refined lies outside of the acceptance range with its lower limit U and its upper limit O. To this end, the at least one preferably traversing measuring system for acquiring the necessary measurement values $y_{ik\,(i=1,\ldots,n;\,k=1,\ldots,m)}$ according to the invention is integrated in the production process in such a way that the quality number Q is determined before the web-shaped material is treated within the additional refining process. The production process can then be modified and/or prevented or stopped by means of a manual or preferably automatic comparison of this quality number Q with the values empirically established for the production process for the lower limit U on the one hand and for the upper limit O on the other hand.

Determination of the acceptance range with its lower limit U and its upper limit O, possibly with additionally determined monitoring limits $U_1$, $O_1$ and/or special utilization limits $U_2$, $O_2$ beyond which the web-shaped material produced in this way is specially monitored or is earmarked or diverted strictly for limited utilization can take place before initiating the normal production process and/or in an ongoing manner but always apart from the hectic conditions where decisions must be made immediately, for example, in the course of market surveys and lengthy production studies:

Thus test productions are carried out initially while determining the respective quality number Q. The finished products from these test productions can then be analyzed by optional further measurements and the measurement values obtained in this way can be cataloged.

Simultaneously, the finished products from the test productions can be presented to possible customers to learn their opinion of the products. Preferably, these individual opinions are also cataloged.

Based on the measurement values and customer evaluations obtained in this way, the limiting values U and O for the acceptance range, possibly including values $U_1$, $O_1$, $U_2$ and $O_2$, are determined and then used for the subsequent ongoing normal production as decision values for acceptance, monitoring and/or special utilization.

It will be apparent to use the one value in particular, usually the upper limiting value O or the additional upper values $O_1$ and $O_2$, as critical value with respect to poor quality for interrupting production or as an indicator for taking immediate action in production, whereas usually the lower limiting values U and/or additional values $U_1$ and $U_2$ are used as indications of especially high quality which either make it seem advisable to take action in production or allow a utilization of correspondingly finished, especially good products for special uses.

It is highly preferable that as additional refining process the method proposed herein for the production and/or processing of a web-shaped material, particularly paper, with the at least one preferably traversing measuring system includes coating the web-shaped material at least once with a composition, wherein the composition is selected from the group including printing ink, coating color, varnish, and extrusion composition.

It is highly preferable that the method proposed herein for the production and/or processing of a web-shaped material, particularly paper, is carried out on at least two independent machines. The first machine is then used for the production of the web-shaped material, while the second machine is used for refining the web-shaped material which has been produced beforehand. In a particularly preferred case such as this, this second machine is selected from the group including printing machine, coating machine, varnishing machine and extrusion machine. A second machine of this type can be operated within the same firm as the first machine, but can also be operated in a client firm or in the firm of any licensee. The measuring system according to the invention can be used within the first machine and/or within the second machine.

The following are particularly taken into consideration as measuring system:
  systems for determining the thickness,
  systems for determining the basis weight of the entire web-shaped material and/or coating thereof, and
  systems for determining the relative moisture and/or absolute moisture
but without limiting thereto within the meaning of the present invention.

The present invention will be further described with reference to an example.

In order to form a pulp, a mixture of bleached softwood sulfate pulp and eucalyptus pulp is put in a dissolver together with water until a solids content of, in this case, 4.2% is reached. The pulp contains as additional ingredients, for example, pigments in typical amounts and caustic soda. The finished pulp is ground and then introduced with further ingredients such as sizing solutions into a paper machine which produces a raw paper web with a basis weight of 42 g/m$^2$ from this pulp at a web speed of, in this case, 1050 m/sec. The settings for the paper machine are changed within moderation in different directions and then noted in each instance so that a particularly homogeneous raw paper is obtained on the one hand and an inhomogeneous raw paper, in this case striped raw paper, is obtained on the other hand.

Figure 2:
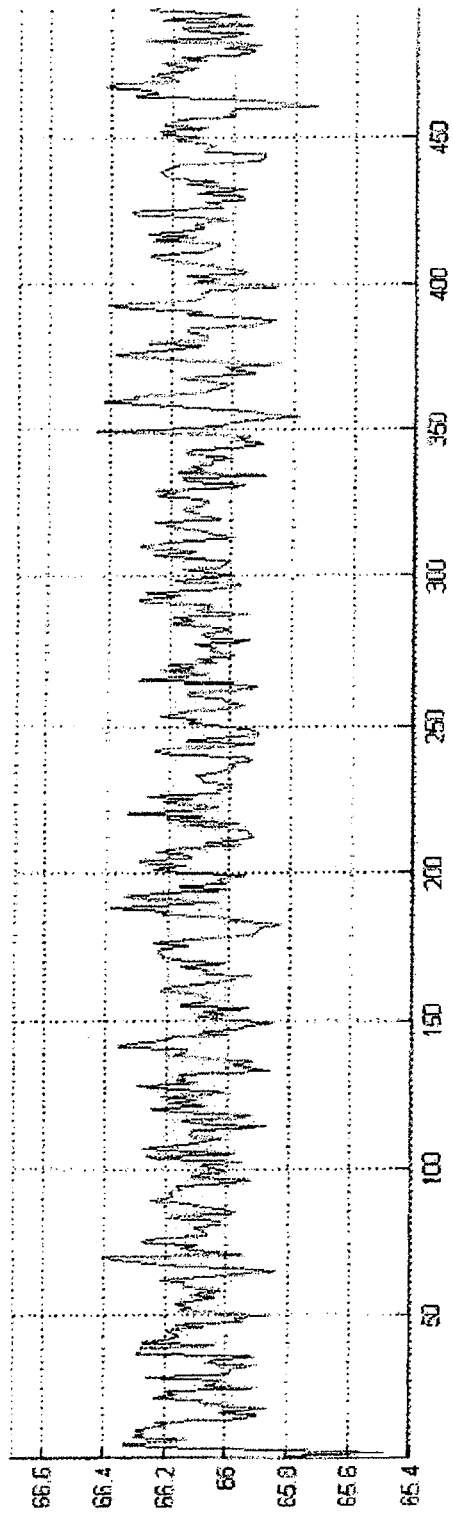
FIG. 2 is a diagram of a second recorded transverse profile.

Using a traversing measuring system, the respective basis weight (bone dry) is determined at n=512 measurement positions transversely over the 5.9-meter width of the raw paper web. Within a time interval $\Delta t$=60 minutes in which a reel is wound with finished raw paper, there are 60 traverses of the measuring system, which means that m=60 different individual measurement values are recorded per measurement position. Numerous samples from the reel of finished raw paper web of particularly homogeneous raw paper on the one hand and conspicuously inhomogeneous, striped raw paper on the other hand are visually inspected a first time by more than one production supervisor in transmitted light and grazing light and related to transverse profiles which are formed from the respective totality of all mean values $\bar{y}_i$ for the 512 measurement positions for each individually considered paper machine setting. It was shown even at this early stage that a quality number Q=2.7 determined according to $$Q = \frac{\sum_{i=1}^{n} |M_i|}{\sum_{i=1}^{n} \frac{\bar{y}_i}{n}}$$ Formula 10 in the paper machine used here for the raw paper in question represents a good raw paper quality that is excellent for further processing, whereas a quality number Q=4.5 with the paper machine used here for the raw paper in question represents a poor quality of the raw paper. FIGS. 1 and 2 show the recorded transverse profiles from the respective totality of all mean values $\bar{y}_i$ for the n=512 measurement positions with m=60 traverses for both of the quality numbers Q=2.7 and Q=4.5 determined according to formula 10.

By means of two extrusion coating apparatuses (curtain coaters), initially an intermediate layer of 6 g/m$^2$ completely covering the raw paper web and subsequently a heat-sensitive recording layer with a basis weight of 2.5 g/m$^2$ are applied to the web of homogeneous raw paper and of striped raw paper in one and the same pass through a coating machine which is used as an independent machine separate from the above-mentioned paper machine. The recipe used to form the intermediate layer contains inorganic pigment (80 wt. %) and latex binder (20 wt. %) as essential components. The essential components of the recipe used to form the heat-sensitive recording layer are listed in the following table 1:

TABLE 1

| Component | Wt. % (bone dry) |
|---|---|
| color former | 9.5 |
| color acceptor | 21.5 |
| sensitizer | 21.5 |
| pigment | 25.0 |
| binder | 17.0 |

After the intermediate layer and heat-sensitive recording layer have been dried in a plurality of floatation dryers in the coating machine, the paper webs coated in this way, with particularly homogeneous raw paper on the one hand and particularly inhomogeneous—in this case, striped—raw paper on the other hand, are subjected to a visual inspection a second time in transmitted light and grazing light and, further, to a tactile inspection while rolled on a reel by feeling the surface of the roll by more than one production supervisor. Whereas the coated paper web with the particularly homogeneous raw paper is considered as an example of good product, the coated paper with the striped raw paper can be considered as an example of defective product. The quality number associated with the coated paper web with the particularly homogeneous raw paper is then correspondingly determined as target quality number Q=2.7; the upper value O in this case is given by the quality numbers for the coated paper web with the striped raw paper at O=4.2. The lower value for especially high-quality raw papers can initially be determined as an estimated value in this case at U=2.2.

The values of U, Q and O can be adjusted over and over again in the course of subsequent productions while taking into account customer responses and/or customer complaints.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for at least one of a production and a processing of a web-shaped material, comprising:
   activating at least one measuring system to record m measurement values $y_{ik\ (i=1,\ \ldots,\ n;\ k=1,\ \ldots,\ m)}$ per measurement position over at least a portion of a width s of web-shaped material at n different measurement positions $x_{i\ (i=1,\ \ldots,\ n)}$ within a fixed time interval $\Delta t$;
   determining a rational quality number Q, wherein a value of the rational quality number corresponds to a quality of the web-shaped material considered acceptable and lies within an acceptance range that is to be empirically determined for the production process, wherein the acceptance range has a lower limit U and an upper limit O, wherein U and O are in each case rational numbers subject to the condition according to:

$$U \leq Q \leq O,\quad \text{Formula 1:}$$

where the value of the quality number Q is calculated as a function of moments $M_i$ according to formula 2, where:

$$Q = f(M_i),\quad \text{Formula 2:}$$

and where the moments $M_i$ are calculated from a function value of a cubic spline function S(x) for the n different measurement positions according to formula 3, where:

$$S(x) = \alpha_i + \beta_i \cdot (x - x_i) + \gamma_i \cdot (x - x_i)^2 + \delta_i \cdot (x - x_i)^3,\quad \text{Formula 3:}$$

where:
   x is a control variable in direction of the width s of the web-shaped material in interval $[x_i, x_{i+1}]$
   $x_{i\ (i=1,\ \ldots,\ n)}$ are the measurement positions corresponding to knots of the cubic spline function, for moments $M_i$, and wherein, based on the measurement values $y_{ik}$ and using the formula 3 as a representation of the function value of the cubic spline function S(x), formula 4 applies to the moments $M_i$, where $$M_i = 2\cdot\gamma_{i\ (i=1,\ \ldots,\ n-1)},\ M_n = 2\cdot\gamma_{n-1} + \delta_{n-1}\cdot(x_n - x_{n-1})_{[42]},\quad \text{Formula 4:}$$

wherein continued production and/or processing of the web-shaped material is controlled based at least in part upon the calculated quality number Q.

2. The method according to claim 1, wherein the measuring system is a traversing measuring system.

3. The method according to claim 1, wherein a function for calculating the quality number Q from the moments $M_i$ corresponds to one of:
   a sum of absolute values of the moments $M_i$ (1-norm),
   a maximum value of the absolute values of all the moments $M_i$ (maximum norm),
   a square root of a sum of squares of the moments $M_i$ (Euclidean norm),
   a variance of the moments $M_i$,
   $\sigma$-rules of any degree of the moments $M_i$ ($\sigma$-value, $2\sigma$-value, $3\sigma$-value, . . . ), and
   a mean of the absolute values of the moments $M_i$.

4. The method according to claim 3, wherein the function for calculating the quality number Q from the moments $M_i$ is a sum of the absolute values of the moments $M_i$ divided by the mean according to formula 10:

$$Q = \frac{\sum_{i=1}^{n} |M_i|}{\sum_{i=1}^{n} \frac{\bar{y}_i}{n}}.\quad \text{Formula 10}$$

5. The method according to claim 1, further comprising:
   performing an additional refining process that is halted when the quality number Q for the web-shaped material to be refined lies outside of the acceptance range with lower limit U and upper limit O.

6. The method according to claim 5, wherein the additional refining process includes coating the web-shaped material at least once with a composition, wherein the composition includes at least one of a printing ink, a coating color, a varnish, and an extrusion composition.

7. The method according to claim 6, wherein the method is carried out on at least two independent machines, of which a first machine is used for producing the web-shaped material and a second machine is used for refining the web-shaped material which has been produced beforehand.

8. The method according to claim 1, wherein the at least one measuring system is a system for determining a thickness.

9. The method according to claim 1, wherein the at least one measuring system is a system for determining a basis weight.

10. The method according to claim 1, wherein the at least one measuring system is a system for determining a moisture.

11. The method according to claim 1, wherein the web-shaped material includes paper.

* * * * *